United States Patent [19]

Gabriel

[11] Patent Number: 4,913,132
[45] Date of Patent: Apr. 3, 1990

[54] MYRINGOTOMY INSTRUMENT

[76] Inventor: Noble Gabriel, 7 Derringer Rd., Chelmsford, Mass. 01824

[21] Appl. No.: 254,312

[22] Filed: Oct. 6, 1988

Related U.S. Application Data

[63] Continuation of Ser. No. 890,485, Jul. 25, 1986, abandoned.

[51] Int. Cl.$^4$ .............................................. A61B 1/22
[52] U.S. Cl. .......................................... 128/9; 606/14; 606/17; 128/395
[58] Field of Search ...................... 128/4, 6, 9, 303.14, 128/303.15, 303.1, 395, 398; 353/101; 350/255; 372/101

[56] References Cited

U.S. PATENT DOCUMENTS

| | | | |
|---|---|---|---|
| 2,098,702 | 11/1937 | Gaghom | 128/9 |
| 2,184,351 | 12/1939 | Langsher | 350/255 |
| 3,020,912 | 2/1962 | Chester | 128/9 |
| 3,417,754 | 12/1968 | Smart | 128/395 |
| 3,659,613 | 5/1972 | Bredemeier | 128/395 |
| 3,843,865 | 10/1974 | Nath | 128/395 |
| 3,865,113 | 2/1975 | Sharon et al. | 128/303.1 |
| 3,978,850 | 9/1976 | Moore et al. | 128/9 |
| 3,982,541 | 9/1976 | L'Esperance, Jr. | 128/303.1 |
| 4,006,738 | 2/1977 | Moore | 128/9 |
| 4,106,493 | 8/1978 | Proctor et al. | 128/9 |
| 4,211,229 | 7/1980 | Warster | 128/6 |
| 4,366,811 | 1/1983 | Riester | 128/9 |
| 4,608,980 | 9/1986 | Aihara | 128/303.1 |
| 4,622,967 | 11/1986 | Schachar | 128/9 |
| 4,671,273 | 6/1987 | Lindsey | 128/303.1 |

FOREIGN PATENT DOCUMENTS 0164751 12/1985 European Pat. Off. .......... 128/303.1

OTHER PUBLICATIONS

Soderbery et al.; "Myringotomy Made by CO$_2$ Laser An Alternative to the Ventilation Tube"; 1984; pp. 335-341.

Wilpizeski et al.; "Otological Applications of Lasers: Basic Background"; pp. 185-192.

Goode; "CO$_2$ Laser Myringotomy"; 1982; pp. 420-423.

Goode; "For Serious Otitis Media, Laser Myringotomy?"; 1979; p. 709.

Schwartz; "Myringotomy: A Neglected Office Procedure"; 1979; pp. 102-108.

Gates; "The Role of Myringotomy in Acute Otitis Media"; 1984; pp. 391-397.

Laxford et al.; "Myringotomy and Ventilation Tubes: A Report of 1568 Ears"; 1982; pp. 1293-1297.

Primary Examiner—Edward M. Coven
Assistant Examiner—Mark S. Graham
Attorney, Agent, or Firm—Pearson & Pearson

[57] ABSTRACT

A hand held myringotomy instrument comprises an otoscope and an attached laser beam generator section. The laser beam generator section comprises a portion for moving the laser beam generator of the section along the laser beam axis, in order to adjust the position of the focus of the laser beam nearer, or father from the instrument. Preferably, the moving portion includes an inner sleeve carrying the generator and an outer sleeve respectively inside and outside of a tube connected to the otoscope. A pair of elements diametrically opposed attached to the inner tube project through longitudinal slots diametrically opposed in the tube and are externally threaded to mesh with internal threads on the outer sleeve. The slots restrict the motion of the elements to axial motion. Collars restrict the motion of the outer sleeve to rotational motion. Thus, rotation of the outer sleeve causes longitudinal motion of the elements which moves the laser beam lens system carried by the inner sleeve axially along the laser beam axis as desired.

5 Claims, 1 Drawing Sheet

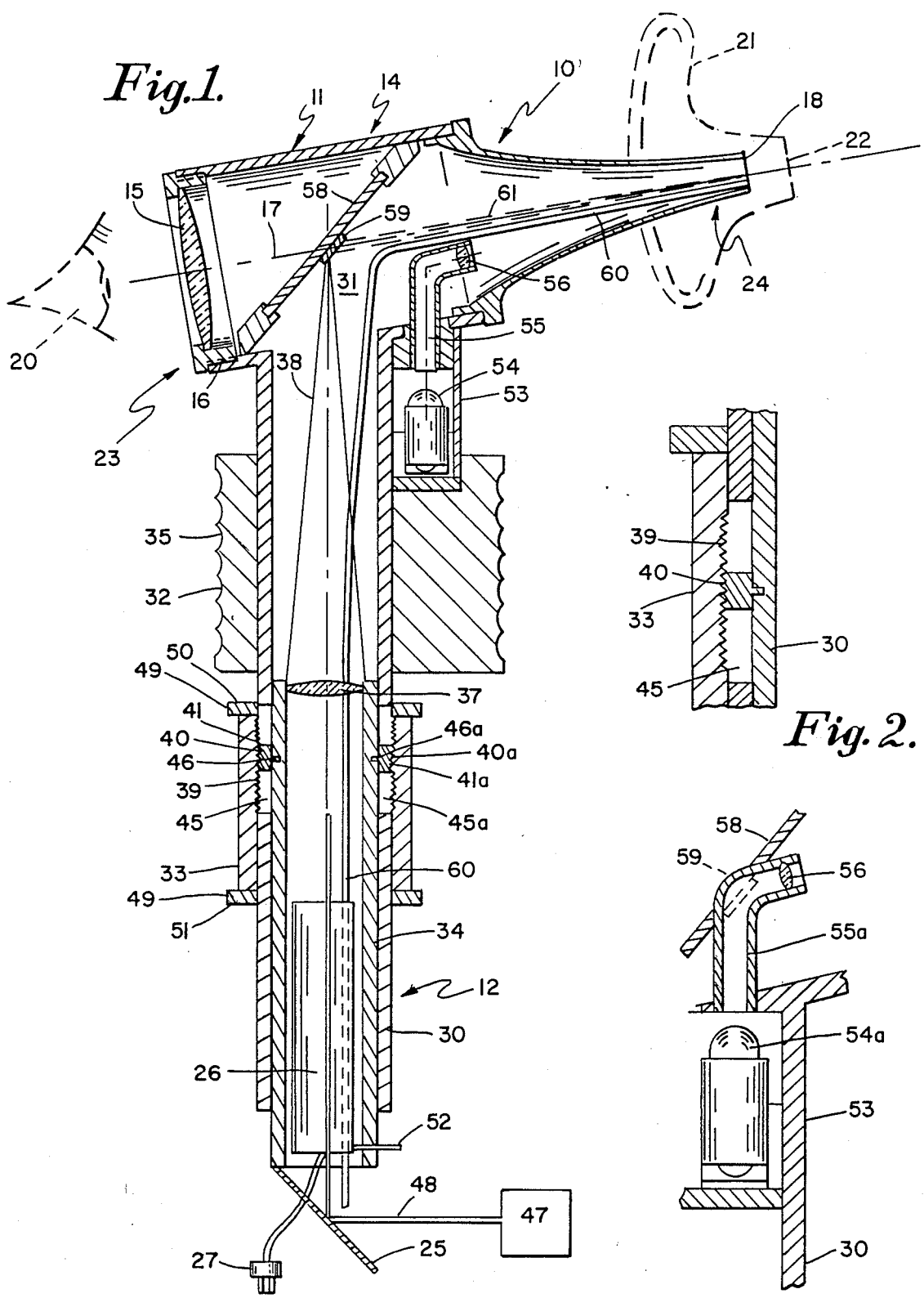
Fig.1.
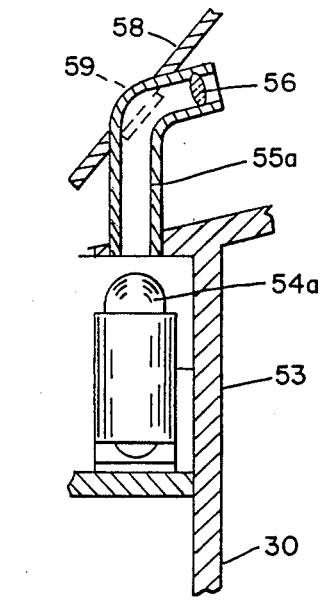
Fig.2.
Fig.3.

MYRINGOTOMY INSTRUMENT

This is a continuation of Ser. No. 890,485, filed 7/15/86, now abandoned.

FIELD OF THE INVENTION

The invention relates generally to otoscopes and the like, and more particularly to an instrument for performing myringotomies.

BACKGROUND OF THE INVENTION

One of the preferred treatments for serous otitis media (SOM) is myringotomy, particularly in cases in which treatment with antibiotics have failed to overcome the underlying infection. One method of performing myringotomy is by incision with a knife, for example, as described by Dr. Richard H. Schwartz in "Myringtomy: A neglected Office Procedure", in AFP for Dec. 1979. Recently there have been cases in which the myringotomy is performed by using a laser. See also the article in *Pediatric Annals* entitled "The Role of Myringotomy in Acute Otitis Media" by George A. Gates, dated May 5, 1984, p. 391; and an article by Luxford, et al, entitled "Myringotomy and Ventilation Tubes: A Report of 1,586 Ears" in "Laryngoscope 92, Nov., 1982, p. 1293. Recently it has been suggested that the myringotomy may be accomplished by the use of a laser. For example, as described by Richard L. Goode in *Laryngoscope* 92: Apr., 1982, p. 420; and also in a note in *Journal of American Medical Association*, v. 242, No. 88, Aug. 24–31, 1979, p. 709; and in "Otological Applications of Lasers: Basic Background" by Chester Wilpizeski, et al. Further, "Myringotomy Made by $CO_2$ Laser—an Alternative to the Ventilation Tube?", and experimental study by Solderberg, et al in Acta Otolaryngol (Stockh) 1984, 97: 335–341.

Also, of possible interest note the following U.S. Pat. Nos. 2,098,702 to Gagnon, Nov. 9, 1937 for Diagnostic Instrument, disclosing a hand held otoscope with a light source for ear examination; 3,020,912 to Chester, Feb. 13, 1962, for Motor Driven Surgical Knife which describes a motor driven knife for performing myringotomy.

Also, the following: U.S. Pat. No. 3,865,114, Feb. 11, 1974 to Sharon, for "Laser Device Particularly Useful as a Surgical Instrument" which describes a surgical laser with a mechanical shield to prevent excess radiation; U.S. Pat. No. 3,982,541 to L'Esperance, Jr., Sept. 28, 1976, for Eye Surgical Instrument which describes the use of a carbon dioxide ($CO_2$) laser for surgically removing surface portions of an eye, such as cataract tissue; U.S. Pat. 4,006,738 to Moore, Feb. 8, 1977, for Otoscope Construction which describes a halogen lamp for providing illumination for an otoscope; U.S. Pat. No. 4,106,493 to Proctor, et al, Aug. 15, 1978, for "Biphasic Otoscopic Air Stimulator for Performing Clinical Caloric Tests" describing an instrument and method of testing by bathing the tympanum and surrounding external tissue in fluid of predetermined temperature; U.S. Pat. No. 4,211,229 to Wurster, July 8, 1980, for Laser Endoscope, which describes the insertion of a laser and lens system in an endoscopic sheath; and U.S. Pat. No. 4,366,811 to Riester, Jan. 4, 1983, for Otoscope with Ejector Mechanism which describes an otoscope with a readily ejected ear funnel.

SUMMARY OF THE INVENTION

According to the invention, an otoscope and a laser beam generator are combined in a single instrument suitable for holding in the hand. The laser is rigidly connected to the otoscope. A reflector is provided arranged in the otoscope diagonally to the optical axis of the otoscope, and to the optical axis of the laser to reflect the laser beam along the line of sight of, and toward the distal end of the otoscope. Therefore, the operator or surgeon who is preparing to perform a myringotomy can view the operating field through the otoscope, and at the same time observe the effects of the laser beam surgery. The laser beam generator is adjustable in the tube in which it is held axially for adjusting the proper place of focus, rather than adjusting the focal length, thereby achieving a close adjustment.

By making the instrument hand-held, it may be used more accurately, and with the adjustment described with better control than manipulating separate instruments or adjusting focal length. The reflector may comprise ground and polished quartz, or a stainless steel element polished to a mirror surface. The otoscope may include means for providing a dispersed illumination of the viewing area, and if desired a suction tube for withdrawing exudate, or the like.

DESCRIPTION OF THE DRAWINGS

The various objects, advantages and novel features of the invention will be more fully understood from a reading of the following detailed description when read in connection with the accompanying drawing, in which like reference numerals refer to like parts, and in which:

FIG. 1 is a central longitudinal cross-sectional view, partly schematic, of the combined otoscope and laser instrument of the invention;

FIG. 2 is a partial sectional view, slightly enlarged, of a detail of FIG. 1, illustrating the adjustment means; and FIG. 3 is an alternative to means of FIG. 1 for providing diffuse illumination for the otoscope of FIG. 1.

DETAILED DESCRIPTION OF DRAWING

Referring to FIG. 1, the myringotomy instrument 10 comprises an otoscope 11, and a laser beam generator section 12, which may be a carbon dioxide ($CO_2$) laser or other, for example, an Argon laser. The otoscope comprises a housing 14, ocular lens at lens systems 15 in the housing 14, and a threaded adjustment 16 in the housing for moving the ocular lens 15 forward or back, in the direction of the optical axis 17 of the lens 15. The housing leads from the lens 15 in the proximal end 23 toward the distal end 24, where the housing terminates in a speculum, or opening, 18, which may, if desired, be removable by any suitable expedient, here shown as simply attached by a slight frictional and inherent spring attachment. At its distal end 24, the speculum terminates in an opening 18. Shown in dashed lines are the human eye 20 of the operator, and the ear lobe 21 of a patient as they might appear with the instrument in place. The tympanum of the ear which is to be the subject of the myringotomy is shown at 22.

The laser section 12 comprises a laser beam generator and power source indicated schematically at 26 to generate the laser beam which may be batteries within the tube, or a power converter for converting the usual ac electrical supply to the requisite laser supply, such as dc, and is therefore, supplied by the usual plug 27 for connection to any suitable outlet. A tube 30 contains the generator 26, and the tube 30 is rigidly connected to the otoscope housing 14. The housing 14 has an opening at 31 to receive the beam 38 from the laser generator 26. A mirror 25 may be provided for use with an external laser beam generator and/or a power source 47 and external laser beam 48.

A plastic hand grip 32 may surround and be attached to the tube 30, and furnished with external grooves 35 so that the hand may fit comfortably around the grip. The tube 30 carries an outer sleeve 33, and an inner sleeve 34. The inner sleeve 34 (see also FIG. 2) carries the generator 26 within the tube 30. A laser lens system indicated by the single lens 37 is carried also by the inner sleeve 34 as part of the laser generator 26. The outer sleeve 33 is internally threaded as at 39 to match and mesh with similar threads 40 and 40a on the outer surfaces of a pair of traveling elements 41 and 41a on diametrically opposite sides of tube 30. Although one element would be operable, the two opposite elements 40 and 40a tend to avoid possible canting of the inner sleeve 34, and thus enable smoother operation. The inner sleeve 34 slides inside the tube 30 in a close sliding fit. On diametrically opposite sides in tube 30, a pair of longitudinal, axial slots 45 and 45a receive respectively the traveling elements 41 and 41a. The elements 41 and 41a may slide only axially longitudinally in the slots 45 and 45a in which they fit closely. Consequently, when the outer sleeve 33 is rotated about the tube 30, the traveling elements 41 and 41a are forced to follow the slots longitudinally. The elements 41 and 41a have projections 46 and 46a inserted, such as by screwing into the inner tube 34. Therefore, as the traveling elements 41 and 41a travel axially, they carry the inner sleeve 34 axially with them. A pair of collars 49 having an upper collar 50, and a lower collar 51, respectively above and below the outer sleeve 33, restrain the outer sleeve 33 from axial motion and permit only rotational motion of the outer sleeve. A switch 52 may actuate the laser generator 26.

A housing 53 may be attached to the tube 30 adjacent the otoscope casing and carries a light source 54 which may supply light to an optical fiber bundle 55, through a lens 56. The bundle carries the light through an appropriate opening in the housing 14, such as at 18, and is faced so that light exiting the bundle is thrown as a diffuse light into the operating area, to enhance the viewing by the operator of the area of the myringotomy.

In the otoscope a strut 58 extending diagonally from top to bottom of the otoscope 14 carries a laser beam reflecting element 59 faced diagonally to intercept the laser beam 38 and deflect the beam toward the opening 18 of the otoscope so that the beam may be focused appropriately for the proposed myringotomy. The element 59 may be an optically ground and polished quartz or stainless steel with a polished reflecting surface.

A flexible suction tube 60 may lead from a suction apparatus into the interior of the otoscope housing through the opening 18, or may lead along the exterior of the otoscope to withdraw any fumes, exudate, or the like in the area.

In operation, the operator or surgeon applies the otoscope in the usual manner to the ear 21 of a patient so that he may view the tympanum 22. The light from the fibers 55 should be adequate to give the operator a view of the tympanum surface. The switch 52 is now actuated and preferably supplies an extremely short burst of the laser beam 38 which has a focal length determined by the lens system 37. The operator may judge from this initial burst which may be of microsecond duration, or the like, and the possible burn which it inflicts preferably without burning through the tissue, whether or not the focal length brings the laser beam onto the tympanum in a desired size, and at the correct place. He then can adjust the otoscope for placement, and adjust the lens system, as described, by rotating the outer sleeve 33 to advance or retard the focal point along the laser beam 61, (after the axis beam reflection) to afford the desired size of spot. By using very fine threads, the adjustment may be very close and fine. The operator may then repetitively actuate the switch to produce the short bursts until he achieves the desired opening in the tympanum.

If desired, a light source may be located adjacent the strut 58 on the tube 30 (as indicated in FIG. 3) as by a light source 54a with optical fiber bundle 55a facing the operating area. Alternatively, both sources 54 and 54a may be employed.

By making the threads 39 very fine, the motion of the lens system 37 may be adjusted very closely. Thus, rather than adjusting the focal length by moving one lens relative to another, the entire lens system is moved, giving a finer, more precise adjustment of the point along the beam axis at which the focal point of the laser beam occurs, and giving finer, more precise adjustment of the size of spot which may be burned by the beam, then by adjusting relative lens locations of the laser beam lens system.

I claim:

1. A hand-held myringotomy instrument comprising:
   an otoscope comprising a housing having a proximal end and a distal end, an optical lens system having an ocular lens at the proximal end and having an optical axis, and a speculum at the distal end, whereby an observer may view through the ocular lens from the proximal end along the optical axis a desired area near and beyond the distal end;
   a tube rigidly connected to the housing;
   a laser beam source for providing a laser beam along a beam path within the tube;
   a lens system for focusing the laser beam at a focal point a certain distance from the laser lens system;
   means for moving the entire laser lens system along the laser beam axis of the laser beam to move the laser beam focal point along the laser beam path;
   a laser beam reflector in the otoscope interposed diagonally in the laser beam path axis and diagonally in the optical lens axis to redirect by reflection the laser beam coincidentally with the otoscope lens system optical axis toward the otoscope distal end, the laser beam leans system focusing the laser beam at a point beyond the otoscope distal end;
   whereby an operator may observe from the proximal end the area at which the laser beam is directed near the distal end of the otoscope and by said moving means adjust the point of focus along the laser beam axis.
   said means for moving the laser beam lens system comprising an inner sleeve carrying the laser beam leans system inside the tube;
   an outer sleeve about the tube internally threaded and restricted to rotation about the tube;

a traveling element fastened to the inner tube and externally threaded to mesh with the outer sleeve internal threads;

the tube having a longitudinal slot within which the elements projects, and said slot restricting the element to axial motion along the tube, whereby rotation of the outer sleeve moves the element axially, and the attached inner sleeve axially thereby to move axially the laser beam lens system carrier by the inner sleeve.

2. A myringotomy instrument as claimed in claim 1 wherein:

said reflector comprises a quartz plate having a polished reflecting surface to reflect the laser beam.

3. A myringotomy instrument as claimed in claim 1 wherein:

said reflector comprises a steel plate having a polished reflecting surface to reflect the laser beam.

4. A myringotomy instrument as claimed in claim 1 further comprising:

a second traveling element fastened to the inner sleeve diametrically opposed to the first element and externally threaded to mesh with the outer sleeve internal threads;

the tube having a second longitudinal slot diametrically opposed to the first slot within which the second element projects, and said second slot restricting the motion of the second element to axial motion along the tube, thereby promoting a balanced axial motion of the inner sleeve.

5. A myringotomy instrument as claimed in claim 1 further comprising:

a light source, and an optical fiber bundle placed in said otoscope to direct diffused light from the bundle toward the distal end of the otoscope.

* * * * *